United States Patent [19]

Tatham et al.

[11] Patent Number: 4,511,801

[45] Date of Patent: Apr. 16, 1985

[54] RADIATION SCANNING AND MEASURING DEVICE

[75] Inventors: Edward J. Tatham; Richard Kravits, both of Bethlehem; John C. Clymer, Riegelsville; Carvel D. Hoffman, Bethlehem, all of Pa.

[73] Assignee: Bethlehem Steel Corporation, Bethlehem, Pa.

[21] Appl. No.: 399,501

[22] Filed: Jul. 19, 1982

[51] Int. Cl.³ ............................................. G01T 1/29
[52] U.S. Cl. ................................ 250/394; 250/358.1; 378/51; 378/147
[58] Field of Search ................. 250/394, 363 S, 358.1, 250/360.1, 366, 505.1; 378/51, 59, 58, 55, 10, 160, 9, 7, 147; 62/259.2, 118

[56] References Cited

U.S. PATENT DOCUMENTS

| | | | |
|---|---|---|---|
| 2,362,911 | 11/1944 | Litton | 62/259.2 |
| 3,562,531 | 2/1971 | Trachevski et al. | 378/55 |
| 3,684,887 | 8/1972 | Hugonin | |
| 3,808,437 | 4/1974 | Miyagawa et al. | 378/54 |
| 3,835,323 | 9/1974 | Kahil | |
| 4,200,800 | 4/1980 | Swift | 378/10 |
| 4,284,895 | 8/1981 | Morgan et al. | 378/9 |
| 4,352,018 | 9/1982 | Tanaka et al. | 250/363 S |

OTHER PUBLICATIONS

R. C. Potter, J. L. Uher, D. C. Clark and L. B. Dauelsberg, "FMIT Beamstop", *IEEE Transactions on Nuclear Science*, vol. NS-28, No. 3, (Jun. 1981), pp. 2821-2822.

Publication "Now Industry Puts the CAT Scanner to Work", *Business Week*, Sep. 21, 1981, p. 124D.

Primary Examiner—Janice A. Howell
Assistant Examiner—Constantine Hannaher
Attorney, Agent, or Firm—John J. Selko

[57] ABSTRACT

A scanning device for examining an object with gamma rays with shielding for protection from radiation and protection of the mechanism from heat by a cooling jacket formed by spaced plates around the object. The shielding is formed by a pair of shutter-halves forming a lead shutter with mechanism to move the shutter-halves toward and away from each other and one of the shutter-halves mounted on a rotating drum which also carries three gamma ray sources. Gamma ray detectors are mounted in a circle concentric and outside the circle of the sources.

6 Claims, 6 Drawing Figures

FIG. I.

RADIATION SCANNING AND MEASURING DEVICE

BACKGROUND OF THE INVENTION

The present invention relates to apparatus for examining and measuring an object by means of penetrating radiation, such as X rays or gamma rays, and more particularly means for continuous rotation of a source of penetrating radiation, means to collimate the beam of radiation, means to maintain the source, collimator and detectors in a stable measurement plane, and shielding means for protection from radiation and protection of mechanism from heat when dealing with hot objects, such for example, as red-hot steel.

Such scanning, examining and measuring devices have been known in the last few years as computer-aided tomography scanners or as CAT scanners. Uses for such CAT scanners beyond the original medical uses of detailed views of the human brain are continually being developed in different industries.

With the radiation required to operate these devices there is always a danger from too intense radiation from a defective radiation source or from an accident to such radiation source.

In addition it is contemplated to use the present device with continuously moving red-hot steel which poses a danger to the comparatively expensive mechanism from the intense heat emitted by the steel moving through the center of the device.

SUMMARY OF THE INVENTION

It is an object of the present invention to provide protection from radiation in a device such as that which is used to examine an object by means of penetrating radiation.

It is a further object to provide this radiation protection should an accident happen to a radiation source in the device by closing off the dangerous section of the device.

It is a further object of the present invention to provide this protection without interference with the operation of the device but to provide it quickly and in a positive manner when and if needed.

Such protection is provided by an adjustable shutter means wherein the shutter is adjustable to open a necessary distance for use of the device and easily closed during an emergency emission.

It is a still further object of the present invention to use the device for the examination of red-hot steel and to protect the mechanism of the device from the intense heat emitted by this hot steel.

The heat is confined for the most part to the section through which the hot steel passes by means of cooling jackets surrounding that section.

The hot steel passes through the center of the device surrounded by radiation sources and numerous detectors with a surrounding cooling jacket between the hot steel and the sources, detectors, and other operating mechanism.

BRIEF DESCRIPTION OF THE DRAWINGS

These and other objects and advantages of the present invention will be apparent from the following description and the accompanying drawings in which.

DESCRIPTION OF THE PREFERRED EMBODIMENT

Figure 1:
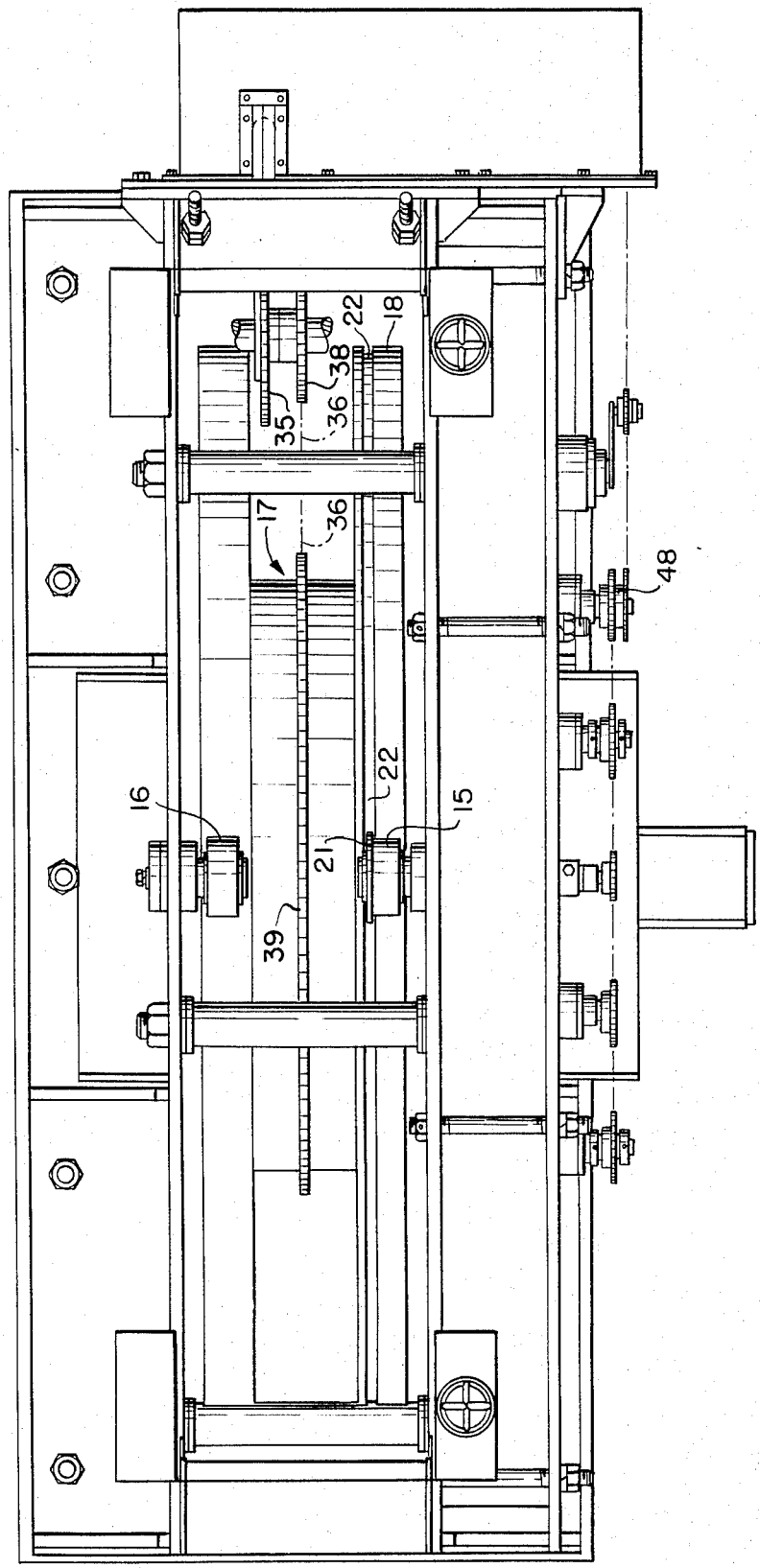
FIG. 1 is a plan view of the scanning device of the present invention.
Figure 2:
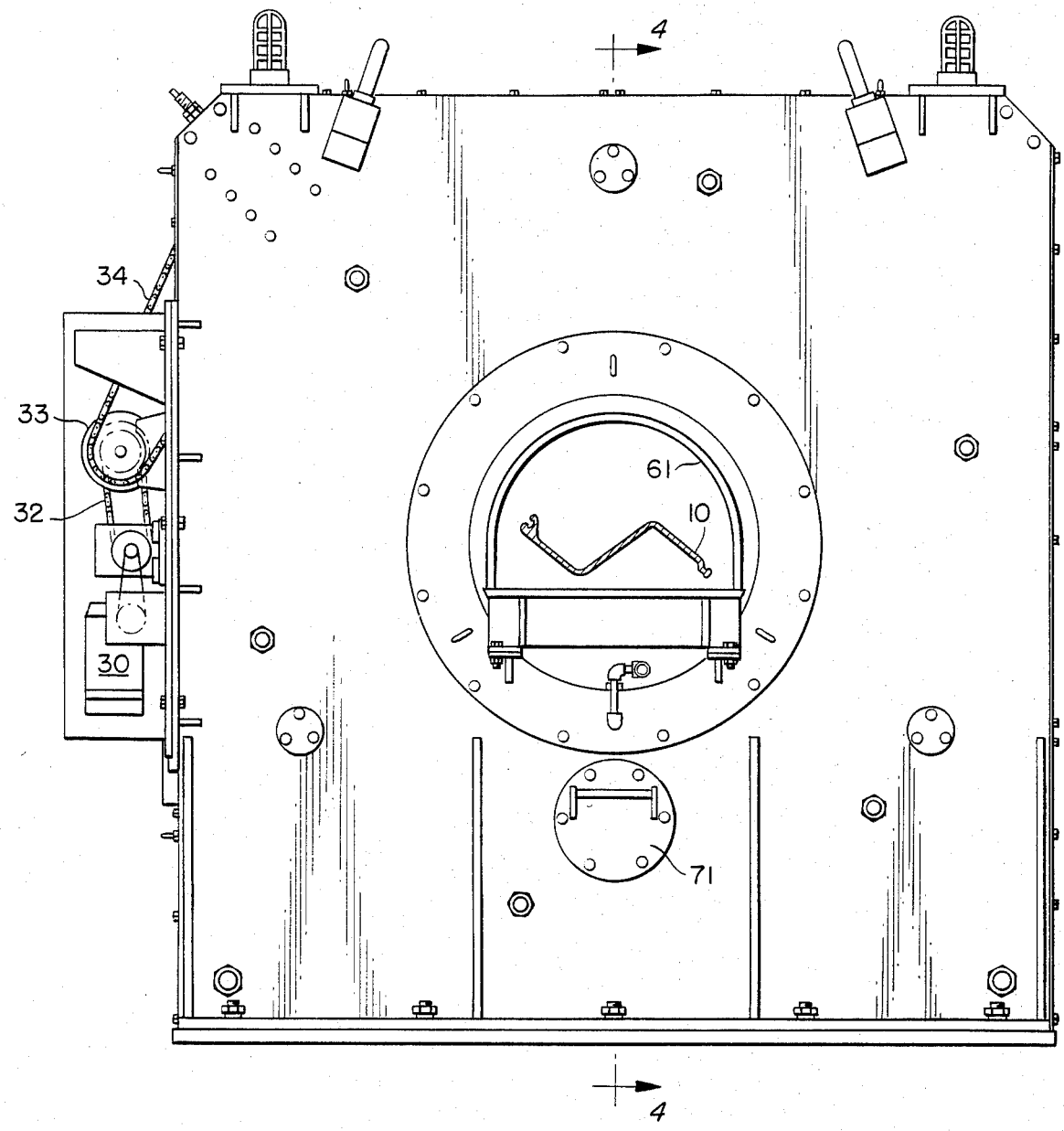
FIG. 2 is an elevation view of the device of FIG. 1 looking at the side opposite from where the radiation sources are located.
Figure 5:
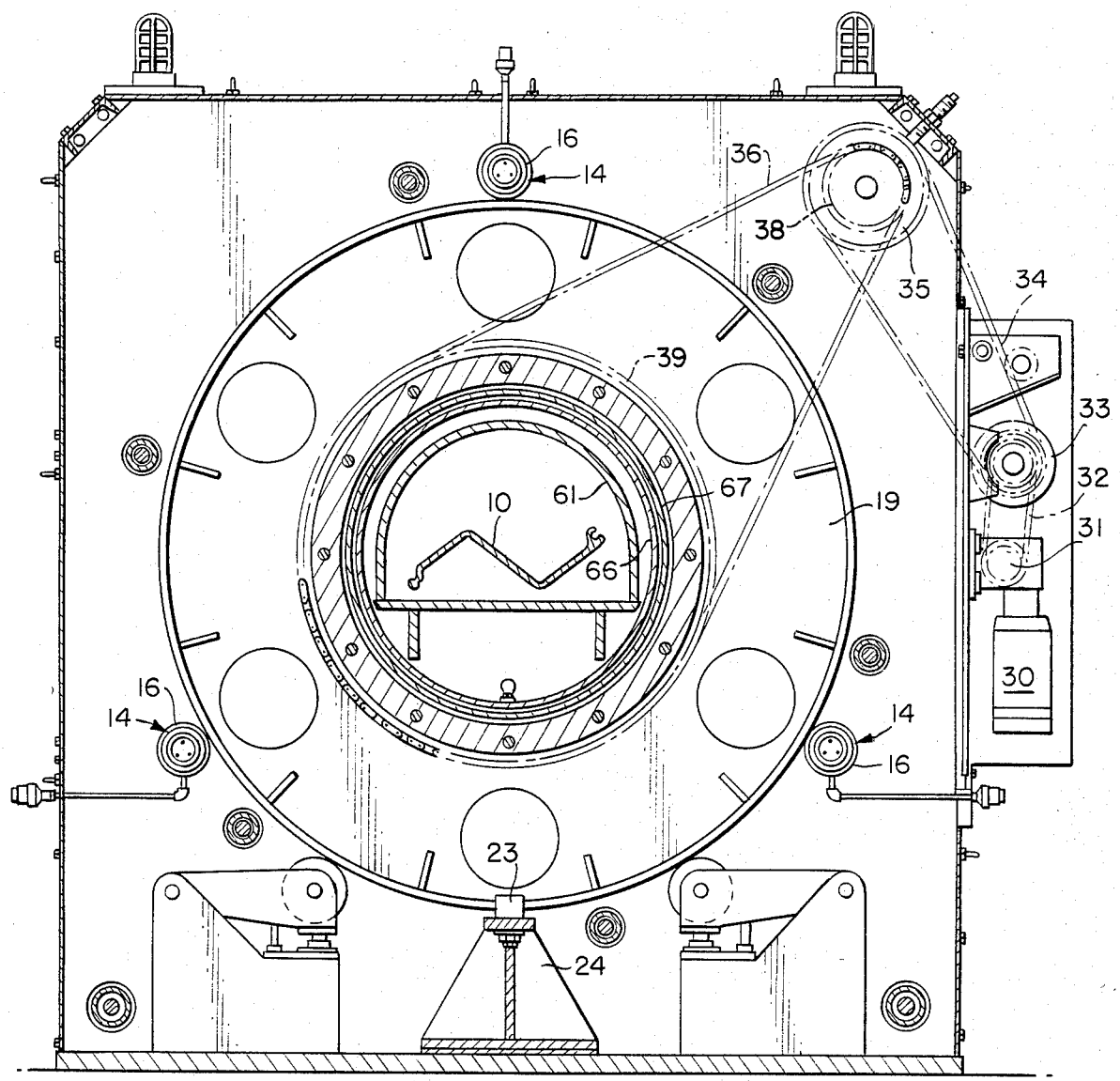
FIG. 5 is a section view along line 5—5 of FIG. 4.

Referring to FIGS. 2 and 5 there is shown a scanning device for examining an object 10 which in the particular instant is a steel sheet piling having extensive length, how long not being of consequence here since the piling or other object 10 is passed through the scanning device. The object 10 is examined and by associated measuring apparatus (not shown) certain characteristics are determined or flaws are noted.

Figure 4:
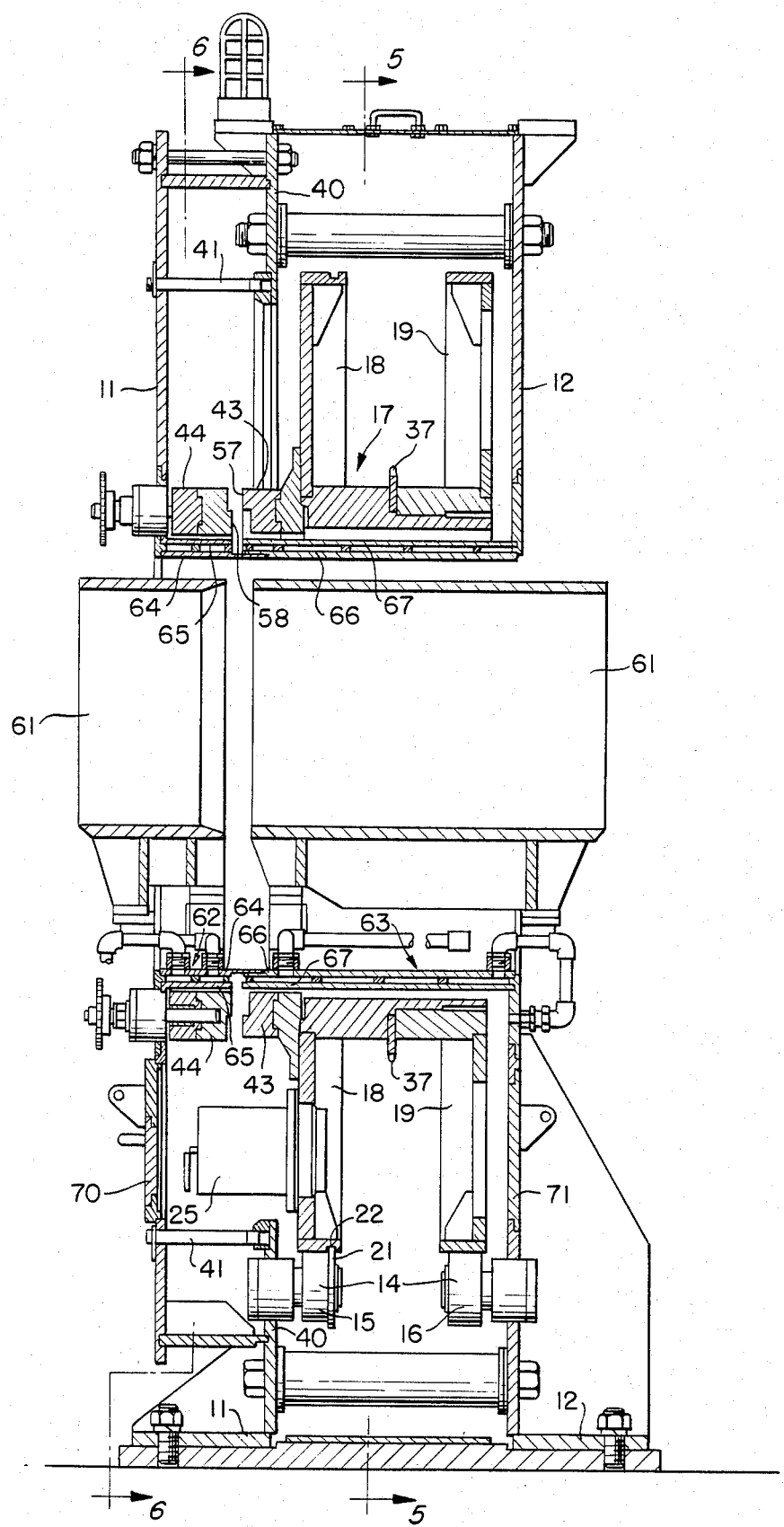
FIG. 4 is a section view through the device along line 4—4 of FIGS. 2 and 3.

Referring to FIG. 4, the scanning device consists of stands 11, 12 which support three pairs of rollers 14 having individual rollers 15 and 16 making up each pair. Rollers 15 are supported by stand 11 and rollers 16 are supported adjacent thereto by stand 12. Pairs of rollers 14 support and laterally guide a rotating drum 17 and are substantially equi-spaced around its periphery.

Rotating drum 17 has flanges 18 and 19 extending therefrom. A practical embodiment for such a rotating drum 17 with flanges 18, 19 may have a diameter measuring eighty six inches. Flange 18 is supported on rollers 15 with a flange 21 on each of rollers 15 riding in notch 22 of flange 18, and flange 19 of rotating drum 17 riding on rollers 16. Prevention of sideward movement or wobble of drum 17 is further controlled by a pair of horizontally adjustable bearings 23, one of which is shown in FIG. 5 supported on a stand 24, which press outward against the inner oppositely facing surfaces of flanges 18, 19 of drum 17. Rollers 15 and 16 as shown in FIG. 4 have been rotated sixty degrees from actual position for clarity with stand 24 omitted, and are located as shown in their positions in FIG. 5 where the stand 24 is also shown.

Figure 6:
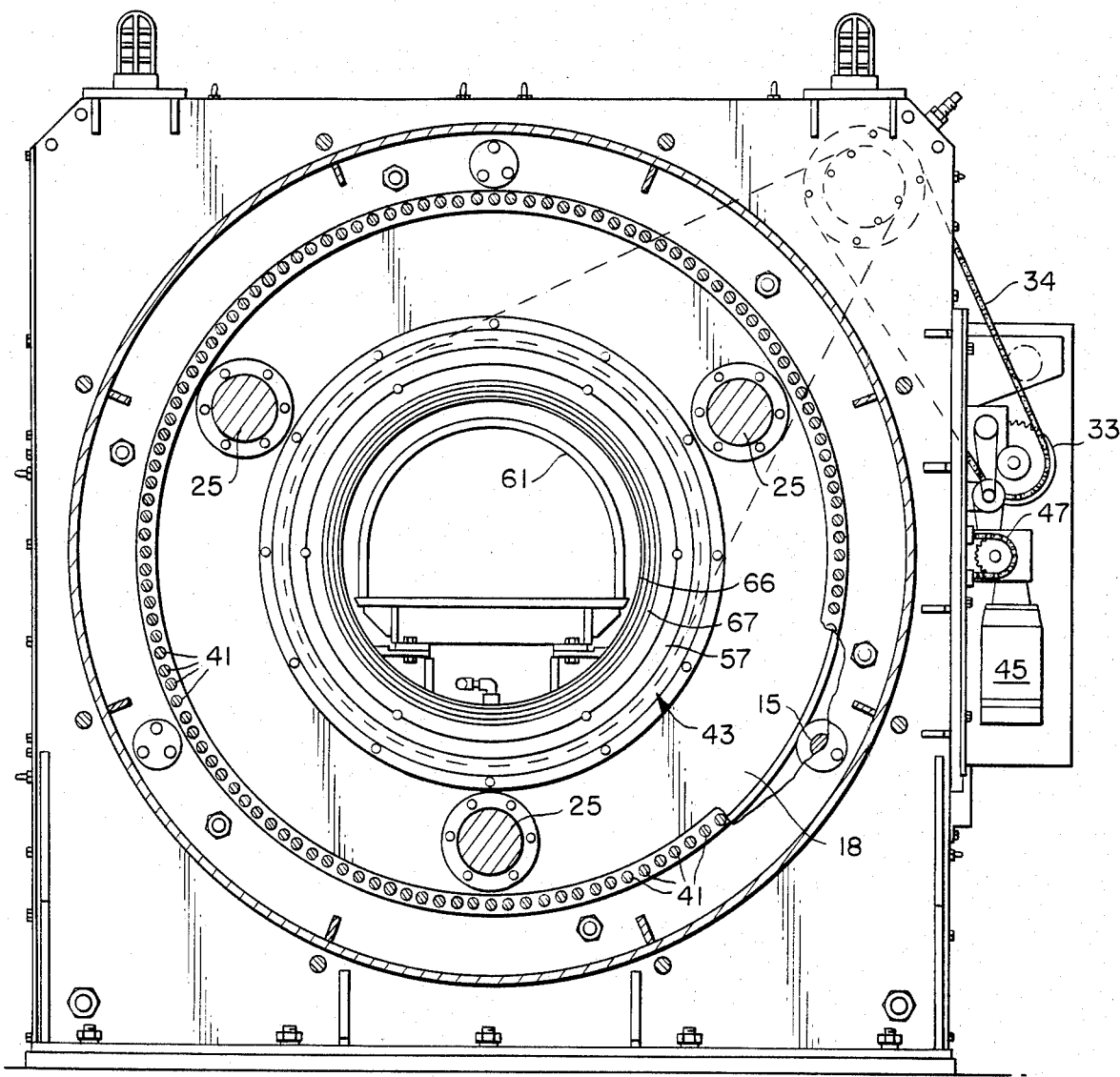
FIG. 6 is a section view along line 6—6 of FIG. 4.

Referring to FIGS. 4 and 6, on the outside of flange 18 there are carried three gamma ray sources 25 equally spaced on a circle concentric with the center of drum 17 and rotatable with drum 17.

Rotating drum 17 is rotated by a variable speed drive 30 and sprocket and chain connections shown in FIG. 5 and to an extent in FIG. 6. Variable speed drive 30 operates sprocket 31, moving chain 32, rotating sprocket 33, which in turn moves chain 34 thereby rotating sprocket 35. Sprocket 35 rotates sprocket 38, being mounted on a shaft common to both. Sprocket 38 thereby moves chain 36. Chain 36 rotates sprocket 39 which is connected to drum 17.

A stationary ring 40 is attached at its periphery to stand 11 this being on the same side of rotating drum 17 to which gamma ray sources 25 are connected. Located between stand 11 and stationary ring 40 are one hundred twenty eight gamma ray detectors 41 horizontally positioned concentric with the center line of drum 17 and outside the circle containing sources 25.

Figure 3:
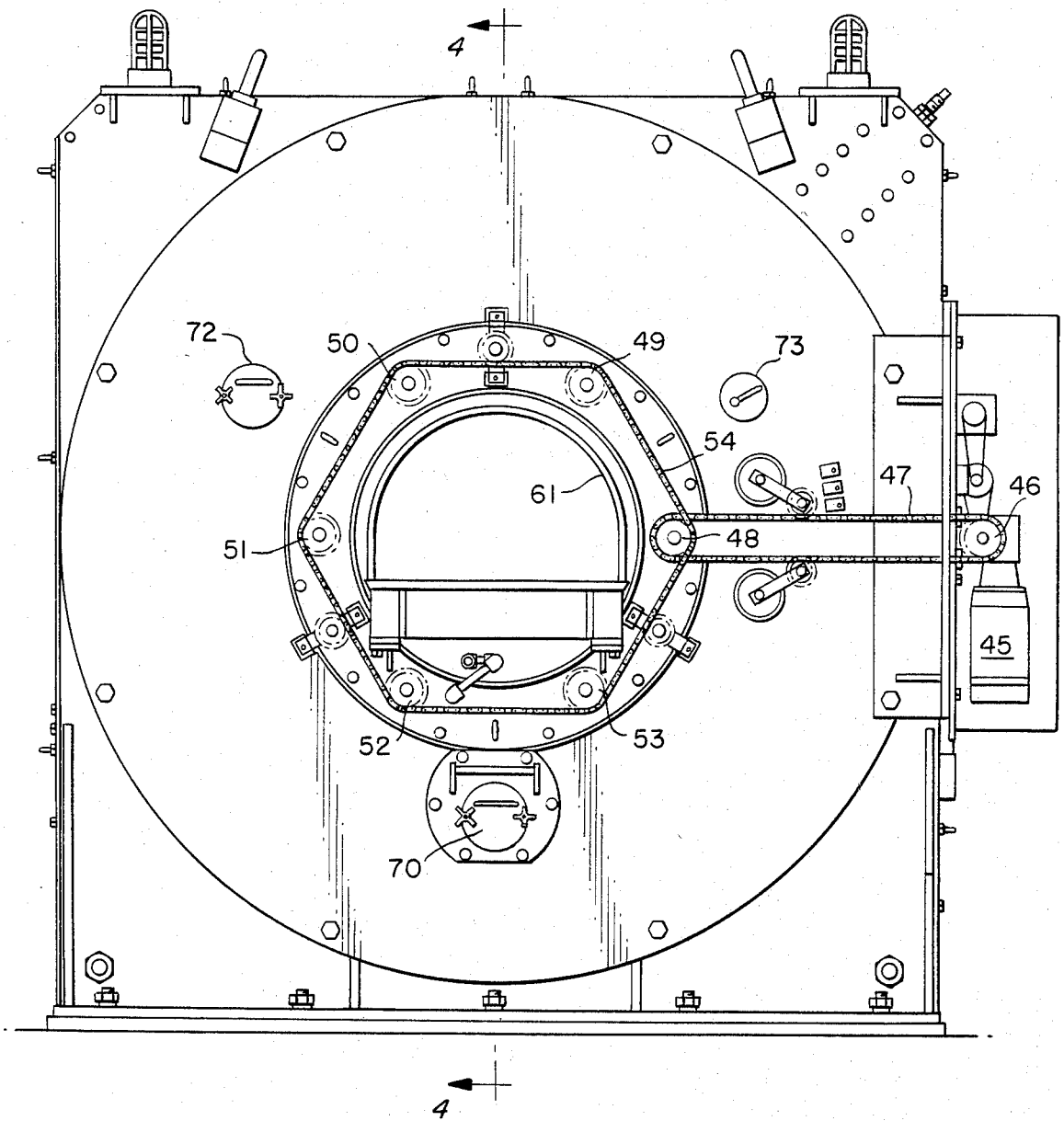
FIG. 3 is an elevation view of the device of FIG. 1 looking at the side on which the radiation sources are located.

Shielding from radiation is provided by the walls of vertical stand 12, the stationary ring 40, the flanges 18 and 19, and a circular lead shutter. The circular lead shutter consists of two halves 43 and 44 provided to shield the area from radiation during normal operation as well as during emergency procedures. During normal operation shutter-half 43 rotates with drum 17 while shutter-half 44 remains stationary. Shutter-half 44 can be moved horizontally by means of motorized drive 45 located alongside variable speed drive 30 and therefore both are not seen in the same side elevation views. Motorized drive 45 and connections to the shutter are shown in FIGS. 3 and 4. Motorized drive 45 is connected to turn sprocket 46, moving chain 47 around sprocket 48. Sprockets 49–53 are all connected by chain 54 to rotate with sprocket 48. The rotation of sprockets 48, 50 and 52 causes rotation of screws extending from each sprocket into shutter-half 44 to move shutter-half 44 toward or away from interfitting shutter-half 43. Sprockets 49, 51 and 53 are idlers, mounted on guide pins which support shutter-half 44. This movement of edge 58 of shutter-half 44 toward and away from edge 57 of shutter-half 43 is used to adjust the width of the gamma ray beam emitted by radiation sources 25. Shutter-half 44 can also be moved horizontally to contact shutter-half 43 wherein edges 57 and 58 are interfitting in order to interrupt the gamma ray beam for shut-down or emergency purposes. The drive 45 can be automatically operated or manually controlled from a remote station.

As a protection from cobble ends from the steel shape which is object 10 being scanned in the scanner device, there are side guards 61 within which object 10 passes as it moves through the opening extending through the center of the scanner device. Since this object 10 is usually a very hot length of steel shape, a further protection is needed for the mechanism of the device from the intense heat emitted. Such protection is provided by a cooling jacket having section 62, 63 which in the case shown in FIG. 4 is a fluid, air or water, cooling jacket. The fluid cooling jacket encloses a tunnel or side guards 61 by spaced apart concentric plates 64, 65 forming cooling jacket section 62, and spaced apart concentric plates 66, 67 forming cooling jacket section 63, with piped fluid inlets and outlets to each of sections 62, 63. Fluid is exhausted into the interior of the apparatus to provide a positive pressure for the exclusion of dust or other foreign matter. The adjacent edges of plates 67 and 65 are spaced apart a distance at least that of the maximum separation of edges 57 and 58 of the shutter-halves 43 and 44 so as not to interfere with the gamma ray beam even at the widest opening of the circular lead shutter. Plates 64 and 66 are connected together by a plate having a reduced thickness in the area where the gamma ray beam passes through the shutter-halves 43 and 44.

The entire device is enclosed and has no external moving parts except for short lengths of sprocket chains. But sources are readily accessible for disarming through covers 70, 72 and 73 or removal through removal covers 70 and 71. Detectors are also easily removed through stationary ring 40.

It will be obvious to those skilled in the art that various changes may be made without departing from the scope of the invention and the invention is not to be considered limited to what is shown in the drawings and described in the specification.

We claim:

1. A scanning device for examining an object with penetrating radiation comprising a rotating source drum having a plurality of gamma ray radiation source devices, a fixed portion of the scanning device surrounding said rotating drum including a plurality of gamma ray radiation detectors mounted on said fixed portion and an adjustable shutter means concentric with said radiation device said adjustable shutter means including a shutter-half connected to said fixed portion and another shutter-half connected to said rotating source drum.

2. The scanning device of claim 1, further characterized by means to move the said shutter-half connected to said fixed portion toward and away from said shutter-half connected to said rotating source drum.

3. The scanning device of claim 2, further characterized by said means to move said shutter-half including a motorized drive, and chain and sprocket means connecting said motorized drive to said movable shutter-half.

4. The scanning device of claim 1, further characterized by each said shutter-half being of ring shape having interfitting shaped adjacent edges.

5. The scanning device of claim 1, further characterized by a fluid cooled jacket surrounding the object between the object and said adjustable shutter means.

6. The scanning device of claim 5, further characterized by said fluid cooled jacket including two pair of spaced plates, each pair having fluid inlet and outlet means connected to allow fluid flow between each pair of spaced plates.

* * * * *